US010161912B2

(12) United States Patent
Nordstrom et al.

(10) Patent No.: US 10,161,912 B2
(45) Date of Patent: Dec. 25, 2018

(54) METHODS AND APPARATUS TO TEST ACOUSTIC EMISSION SENSORS

(71) Applicant: Fisher Controls International LLC, Marshalltown, IA (US)

(72) Inventors: Richard Allen Nordstrom, Marshalltown, IA (US); Shawn William Anderson, Marshalltown, IA (US); Bret Anthony Dahme, Marshalltown, IA (US)

(73) Assignee: Fisher Controls International LLC, Marshalltown, IA (US)

( * ) Notice: Subject to any disclaimer, the term of this patent is extended or adjusted under 35 U.S.C. 154(b) by 132 days.

(21) Appl. No.: 14/992,755

(22) Filed: Jan. 11, 2016

(65) Prior Publication Data

US 2017/0199161 A1    Jul. 13, 2017

(51) Int. Cl.
*G01N 29/14*   (2006.01)
*G01N 29/44*   (2006.01)
*G01N 29/30*   (2006.01)

(52) U.S. Cl.
CPC ............ *G01N 29/14* (2013.01); *G01N 29/30* (2013.01); *G01N 29/4427* (2013.01); *G01N 29/4436* (2013.01); *G01N 2291/101* (2013.01)

(58) Field of Classification Search
CPC .... G01N 29/14; G01N 29/30; G01N 29/4427; G01N 29/4436; G01H 3/005; G01V 13/00
USPC ................. 73/587, 1.82, 590, 592, 593, 584
See application file for complete search history.

(56) References Cited

U.S. PATENT DOCUMENTS

| | | | | |
|---|---|---|---|---|
| 4,011,472 A | * | 3/1977 | Feng | B06B 1/0625 310/328 |
| 4,043,176 A | * | 8/1977 | Graham | G01N 29/2437 73/1.82 |
| 4,043,180 A | * | 8/1977 | Morris | E21B 47/101 340/515 |
| 4,437,332 A | | 3/1984 | Pittaro | |
| 4,519,251 A | | 5/1985 | Dickson | |

(Continued)

FOREIGN PATENT DOCUMENTS

| | | |
|---|---|---|
| JP | S5767853 | 4/1982 |
| JP | H0194258 | 4/1989 |
| KR | 20080102082 | 11/2008 |
| WO | 2017123567 | 7/2017 |

OTHER PUBLICATIONS

International Searching Authority, "International Search Report and Written Opinion", issued in connection with International application No. PCT/US2017/012904, dated May 10, 2017 (13 pages).

(Continued)

*Primary Examiner* — Manish S Shah
*Assistant Examiner* — Rose M Miller
(74) *Attorney, Agent, or Firm* — Hanley Flight & Zimmerman, LLC (57) ABSTRACT

Methods and apparatus to test acoustic emission sensors are disclosed herein. An example apparatus includes a process control device, an acoustic emission sensor coupled to the process control device, where the acoustic emission sensor detects an operational condition of the process control device, and a piezoelectric tuning fork acoustically coupled to the acoustic emission sensor to test the operational condition of the acoustic emission sensor.

20 Claims, 3 Drawing Sheets

(56) References Cited

U.S. PATENT DOCUMENTS

| | | | |
|---|---|---|---|
| 4,567,770 A | 2/1986 | Rumbold et al. | |
| 4,922,754 A | 5/1990 | Horne et al. | |
| 5,005,415 A * | 4/1991 | Holroyd | G01H 1/00 73/577 |
| 5,101,162 A | 3/1992 | Webster et al. | |
| 5,191,796 A | 3/1993 | Kishi et al. | |
| 5,435,168 A | 7/1995 | Granere | |
| 6,016,701 A | 1/2000 | McClelland et al. | |
| 6,672,131 B1 | 1/2004 | Aldal et al. | |
| 8,037,762 B2 | 10/2011 | La Rosa Flores et al. | |
| 8,311,759 B2 * | 11/2012 | Sutherland | F16L 55/48 367/117 |
| 2001/0007203 A1 | 7/2001 | Goodman et al. | |
| 2005/0011278 A1 | 1/2005 | Brown et al. | |
| 2007/0034012 A1 | 2/2007 | Amir et al. | |
| 2010/0089161 A1 | 4/2010 | Taheri | |
| 2010/0218591 A1 | 9/2010 | Rhodes et al. | |
| 2016/0178478 A1 | 6/2016 | Erskine | |
| 2017/0199162 A1 | 7/2017 | Nordstrom et al. | |

OTHER PUBLICATIONS

United States Patent and Trademark Office, "Notice of Allowance," issued in connection with U.S. Appl. No. 15/333,658, dated Apr. 10, 2018, 13 pages.

United States Patent and Trademark Office, "Non-Final Office Action," issued in connection with U.S. Appl. No. 15/333,658, dated Jan. 17, 2018, 14 pages.

Dahme, Bret A., et al., "U.S. Appl. No. 15/333,658," filed Oct. 25, 2016, 36 pages.

United States Patent and Trademark Office, "Non-Final Office Action," issued in connection with U.S. Appl. No. 15/387,341, dated Jan. 19. 2018, 15 pages.

International Searching Authority, "International Search Report and Written Opinion," issued in connection with International Application No. PCT/US2017/057956, dated Jan. 26, 2018, 14 pages.

United States Patent and Trademark Office, "Final Office Action," issued in connection with U.S. Appl. No. 15/387,341, dated Oct. 1, 2018, 15 pages.

\* cited by examiner

METHODS AND APPARATUS TO TEST ACOUSTIC EMISSION SENSORS

FIELD OF THE DISCLOSURE

This disclosure relates generally to acoustic emission sensors and, more particularly, to methods and apparatus to test acoustic emission sensors.

BACKGROUND

Acoustic emission sensors are applied in various industries to monitor an operational status of a device (e.g., a valve or other process control device) to which an acoustic emission sensor is coupled. In these applications, it is important to know whether the acoustic emission sensor is functioning properly and acoustically coupled to the monitored device to ensure that the measurements from the acoustic emission sensor are precise and/or accurate. One known method of testing the functionality of an acoustic emission sensor referred to as a pencil lead break test involves an operator or technician breaking lead from a mechanical pencil adjacent the acoustic emission sensor. Another known test involves using piezoelectric sensors in reciprocity mode (i.e., using the piezoelectric sensors as pulse emitters instead of receivers). However, these known tests do not meet the reproducibility and/or practical implementation requirements needed to properly assess the acoustic emission sensor and can cause an operator or technician to improperly assess the functionality of the acoustic emission sensor.

SUMMARY

An example apparatus includes a process control device, an acoustic emission sensor coupled to the process control device, where the acoustic emission sensor detects an operational condition of the process control device, and a piezoelectric tuning fork acoustically coupled to the acoustic emission sensor to test an operational condition of the acoustic emission sensor.

An example method includes providing an electrical signal to a piezoelectric tuning fork to cause the piezoelectric tuning fork to produce an acoustic signal, measuring, using an acoustic emission sensor, the acoustic signal, and comparing the measured acoustic signal to data representing a reference acoustic signal to determine a deviation between the measured acoustic signal and the reference acoustic signal.

BRIEF DESCRIPTION OF THE DRAWINGS

The figures are not to scale. Wherever possible, the same reference numbers will be used throughout the drawing(s) and accompanying written description to refer to the same or like parts.

DETAILED DESCRIPTION

The apparatus and methods described herein can be used in a process control system to test an operational condition of an acoustic emission sensor coupled to a process control device within the process control system. More specifically, the apparatus and methods described herein include a piezoelectric tuning fork coupled to the process control device adjacent the acoustic emission sensor. The piezoelectric tuning fork is operative to emit an acoustic signal to check the functionality of the acoustic emission sensor via a controller that compares a measured acoustic signal to a reference acoustic signal (e.g., an acoustic signal representative of a known good operational condition of the acoustic emission sensor). Thus, the disclosed apparatus and methods may be used to test an acoustic emission sensor to determine the operational condition of the acoustic emission sensor. For example, the disclosed methods and apparatus may be used to determine if the acoustic emission sensor is functioning and properly acoustically coupled to the process control device. Additionally, the disclosed methods and apparatus may indicate if the remainder of the acoustic measurement chain (e.g., a data acquisition system, the piezoelectric tuning fork, cables and/or other communication devices and systems, etc.) are functioning properly.

In some examples, the acoustic emission sensor monitors an operational condition of a process control device by measuring acoustic emissions from the process control device. Specifically, a piezoelectric tuning fork may be acoustically coupled adjacent the acoustic emission sensor so that the acoustic emission sensor can measure an acoustic signal output by the piezoelectric tuning fork. For example, coupling the piezoelectric tuning fork to the process control device adjacent to the acoustic emission sensor creates an acoustic path between the piezoelectric tuning fork and the acoustic emission sensor. In some such examples, a controller or operator workstation determines an operational condition of the acoustic emission sensor by comparing an acoustic signal measured by the acoustic emission sensor to a reference acoustic signal. If the measured acoustic signal is within a threshold range of the reference acoustic signal, the acoustic emission sensor is operational and properly acoustically coupled to the process control device. Alternatively, if the measured acoustic sensor is not within the threshold range of the reference acoustic signal (i.e., a change occurred in the measured acoustic signal), the acoustic emission sensor is either not properly coupled to the process control device or otherwise not functioning properly. In such examples, an alert may be sent to an operator (e.g., via an operator workstation) to indicate that the acoustic emission sensor is not operational or operating properly.

Figure 1:
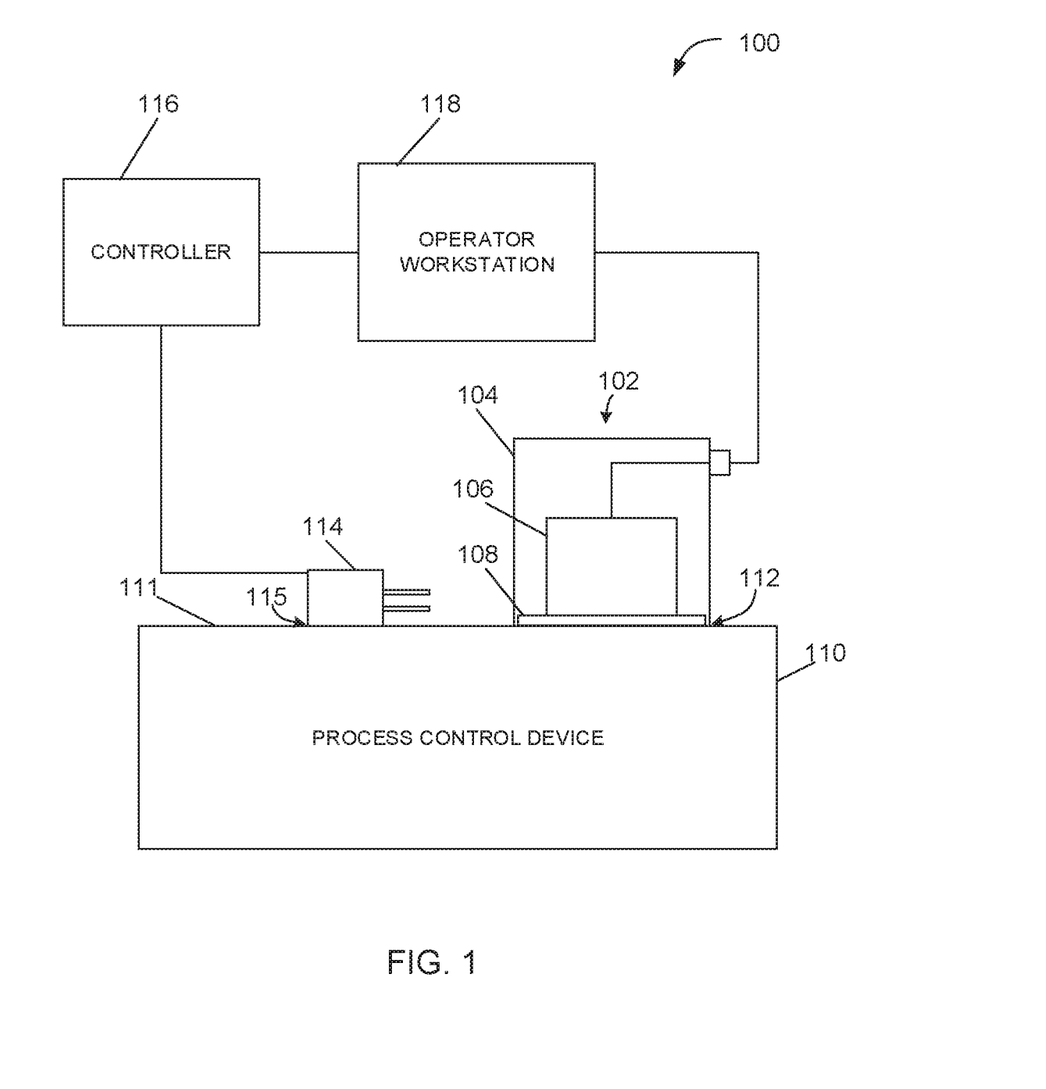
FIG. 1 is a diagram of an example apparatus that may be implemented to test an operational condition of an acoustic emission sensor.

FIG. 1 is a diagram of an example apparatus 100 that may be implemented to test an operational condition of an acoustic emission sensor 102. The acoustic emission sensor 102 may be, for example, a commercially available acoustic emission sensor 102 (e.g., a Vallen Systeme acoustic emission sensor). In some examples, the acoustic emission sensor 102 includes a housing 104 and a piezoelectric element 106 disposed in and/or at least partially surrounded by the housing 104. The acoustic emission sensor 102 measures acoustic signals and transmits the measured acoustic signals using an analog communication interface. The piezoelectric element 106 may be operative to detect mechanical movement resulting from an acoustic signal. For example, the piezoelectric element 106 of the acoustic emission sensor 102, which may be coupled to a valve or pipe, is operative to detect leaks in the valve or pipe. The example acoustic emission sensor 102 also includes a wear plate 108 coupled to the housing 104. The wear plate 108 is at least partially surrounded by the housing 104 and protects (e.g., prevents damage to) the piezoelectric element 106. In some examples, other components (e.g., an electrode, damping material, etc.) may also be disposed within the housing 104.

The example apparatus 100 includes an example process control device 110, which may be a valve, a pipe, or any other process control device. The acoustic emission sensor 102 is coupled to a surface 111 of the process control device 110 and is operative to detect leaks in the process control device 110 (e.g., a valve or a pipe), monitor the structural health of the process control device 110, and detect any other events and/or operational conditions related to the process control device 110. The acoustic emission sensor 102 is coupled to the surface 111 via the wear plate 108. To facilitate acoustic coupling, the acoustic emission sensor 102 may be coupled to the surface 111 of the process control device 110 using a coupling agent or layer 112 such as, for example, a liquid, a gel, or any other suitable coupling agent operative to acoustically couple the acoustic emission sensor 102 to the surface 111 of the process control device 110. Using a liquid or gel as the coupling layer 112 improves the acoustic coupling of the acoustic emission sensor 102 to the process control device 110 by decreasing the amount of air gaps that would otherwise occur between the wear plate 108 and the surface 111 of the process control device 110. Alternatively, the coupling agent or layer 112 may include a glue or partial glue-filler combination capable of providing stable acoustic coupling for long term use.

In the illustrated example apparatus 100, a piezoelectric tuning fork 114 is coupled to the process control device 110. The piezoelectric tuning fork 114 may be a quartz tuning fork (e.g., a quartz resonator) having a high quality (Q) factor. In the example apparatus 100 described herein, the piezoelectric tuning fork 114 is coupled to the surface 111 of the process control device 110 adjacent the acoustic emission sensor 102. In some examples, the piezoelectric tuning fork 114 is coupled to the process control device 110 via another coupling agent or layer 115 (e.g., a liquid or gel) similar to the coupling agent or layer 112 used to couple the acoustic emission sensor 102 to the process control device 110. Coupling the piezoelectric tuning fork 114 to the surface 111 of the process control device 110 adjacent to the acoustic emission sensor 102 creates an acoustic path between the piezoelectric tuning fork 114 and the acoustic emission sensor 102. For example, the acoustic signal output by the piezoelectric tuning fork 114 can readily propagate to the acoustic emission sensor 102 via the surface 111 of the process control device 110. In some examples, the type of coupling agent or layer 112, 115 used to couple the acoustic emission sensor 102 and/or the piezoelectric tuning fork 114 to the surface 111 of the process control device 110 affects the quality of the acoustic path. Alternatively, the acoustic emission sensor 102 and/or the piezoelectric tuning fork 114 may be coupled to the process control device 110 without a coupling agent or layer 112, 115 using, for example, a mechanical fastener, a magnetic coupling, etc.

The illustrated example apparatus 100 also includes an example controller 116. The controller 116 is operatively coupled to the piezoelectric tuning fork 114 to provide an electrical signal (e.g., a voltage signal) to the piezoelectric tuning fork 114. The electrical signal (e.g., the voltage signal) is provided (e.g., transmitted) to the piezoelectric tuning fork 114 to produce a specific acoustic output signal. The electrical signal causes the piezoelectric tuning fork 114 to produce an acoustic signal detectable by the acoustic emission sensor 102. In such examples, the acoustic emission sensor 102 measures the acoustic signal output by the piezoelectric tuning fork 114. The acoustic emission sensor 102 may transmit the measured acoustic signal to the controller 116 and/or a second controller (e.g., a data acquisition system). The example controller 116 and/or the second controller may be operative to store data (e.g., measured acoustic signals). Additionally or alternatively, the data may be stored on a network storage device to facilitate remote access. In some examples, the electrical signal (e.g., input voltage signal sent to the piezoelectric tuning fork 114) may be varied to produce different, corresponding acoustic signals (e.g., output acoustic signals from the piezoelectric tuning fork 114). The expected acoustic signal output by the piezoelectric tuning fork 114 is determined based on the electrical signal provided to the piezoelectric tuning fork 114. For example, data associating the electrical signals with acoustic signals output by the piezoelectric tuning fork 114 are stored in a database. In some examples, the data are organized in a table, a chart, a graph, etc. The data may include acoustic reference signals corresponding to the electrical signals and/or the expected acoustic signals output by the piezoelectric tuning fork 114. Additionally, the data may be accessed remotely from an operator workstation such as, for example, an example operator work station 118 described below.

Electrical signals may be communicated to the piezoelectric tuning fork 114 via any suitable wired or wireless connection. In some examples, the electrical signal (e.g., electrical input) is provided over the same connection used to connect the acoustic emission sensor 102 to the database (e.g., to a data logging system). Alternatively, any other suitable means of communicating an electrical signal to the piezoelectric tuning fork 114 may be implemented instead. In some examples, the controller 116 is also communicatively coupled to the process control device 110 via any suitable wired or wireless connection.

In some examples, the example apparatus 100 includes the operator workstation 118. The operator workstation 118 may be operatively coupled to the controller 116 and/or the acoustic emission sensor 102. In some examples, the operator workstation 118 communicates with the controller 116, the acoustic emission sensor 102, and/or any other controllers or data acquisition systems via a wired or wireless communication protocol. For example, the operator workstation 118 may be remotely located (e.g., from a different location miles away) from the controller 116, the acoustic emission sensor 102, and/or any other controllers and may communicate via a wireless protocol to access data, trigger a check of the acoustic emissions sensor 102, and/or perform diagnostic tests if any inconsistencies are detected within the system. The example acoustic emission sensor 102 may transmit measured acoustic signal data using an analog signal. Alternatively, any other suitable form of wired or wireless communication (e.g., analog or digital) may be used. The electrical signal provided to the piezoelectric tuning fork 114 may be designated by an operator via the operator workstation 118 and/or the controller 116. For example, the operator may designate a magnitude and/or frequency of the voltage of the electrical signal sent to the piezoelectric tuning fork 114. Additionally, the operator may designate a time at which to send the electrical signal to the piezoelectric tuning fork 114.

In some examples, the operator designates the times at which the electrical signal is sent to the piezoelectric tuning fork 114 via the operator workstation 118 by defining a testing schedule. Alternatively, the operator can manually send an electrical signal to the piezoelectric tuning fork 114 (e.g., send an electrical signal on demand) via the operator workstation 118 and/or the controller 116 when the acoustic emission sensor 102 is to be tested. The operator may use the operator workstation 118 to create a test schedule to be followed by the controller 116. In some examples, the test schedule indicates a specific time each day at which the controller 116 is to send an electrical signal to the piezoelectric tuning fork 114. In this manner, the electrical signal is transmitted to the piezoelectric tuning fork 114 at the designated time(s) (e.g., the scheduled time(s)) without further input from the operator. In some examples, the schedule indicates that a test of the acoustic emission sensor 102 is performed on a weekly, monthly, or yearly basis. A test and/or measurement of an acoustic signal received by the acoustic emissions sensor may also be triggered by an event in the process control system such as, for example, a valve closing. Transmitting the electrical signal to the piezoelectric tuning fork 114 may include transmitting electrical pulses for a time period specified by an operator. Alternatively, the operator commands the controller 116 to continuously provide the piezoelectric tuning fork 114 with an electrical signal. In such examples, the operator may designate a stop time or provide the piezoelectric tuning fork 114 with an electrical signal (e.g., continuously) until the operator instructs the controller 116 to stop.

The acoustic signal measured by the acoustic emission sensor 102 (e.g., the measured acoustic signal) is compared to data representing a reference acoustic signal. The data representing a reference acoustic signal may be stored in, for example, a table, a chart, or a graph that indicates the expected acoustic signal output by the piezoelectric tuning fork 114 for each possible electrical signal sent to the piezoelectric tuning fork 114. In some examples, the reference acoustic signal is a previous signal (e.g., an initial signal, an original signal) that was output by the piezoelectric tuning fork 114 and measured by the acoustic emission sensor 102. Alternatively, the reference acoustic signal may be equivalent to the acoustic signal output by the piezoelectric tuning fork 114. A deviation between the measured acoustic signal and the reference acoustic signal is determined based on a comparison between the measured acoustic signal and the data representing the reference acoustic signal. In some examples, the deviation is determined by comparing the values of the amplitudes of the reference signal and the measured acoustic signal. The deviation may be represented as a numerical value equivalent to the difference between the two amplitudes or as a percentage difference between the measured acoustic signal and the reference acoustic signal.

A functionality or operational condition of the acoustic emission sensor 102 may be determined or assessed based on the deviation between the measured acoustic signal and the reference acoustic signal. The deviation between the measured acoustic signal and the reference acoustic signal may indicate a preciseness of measurements from the acoustic emission sensor 102 and/or the functionality of the acoustic emission sensor 102. For example, if the deviation between the measured acoustic signal and the reference acoustic signal is greater than a threshold, the acoustic emission sensor 102 may need maintenance, repair or replacement. The acoustic emission sensor 102 may be designated as not functional if the difference between the measured acoustic signal and the reference acoustic signal is more than a certain percentage (e.g., 5%). An alert or alarm may be displayed via the operator workstation 118 indicating that the acoustic emission sensor 102 is malfunctioning. If the difference between the measured acoustic signal and the reference acoustic signal is below the threshold, the acoustic emission sensor 102 may be considered to be functioning properly and does not require repair or replacement. An appropriate message may be transmitted to the operator workstation 118 indicating the operational condition of the acoustic emission sensor 102.

In some examples, the acoustic signal data measured by the acoustic emission sensor 102 is filtered to improve detection of the acoustic signal by the acoustic emission sensor 102. An example filtering technique uses the high quality (Q) factor and narrow band typical of piezoelectric tuning forks to easily filter the acoustic signal from the piezoelectric tuning fork 114 from background acoustic signals and/or vibrations. For example, because the piezoelectric tuning fork 114 has a high Q factor and narrow band, the amplitude of the measured frequency is large with respect to background noise and the piezoelectric tuning fork 114 operates within a narrow band (e.g., range) of frequencies. Thus, due to the high amplitude and narrow band of the frequencies, the signal from the piezoelectric tuning fork is easily discerned with a filter. In some examples, a quality factor is used to determine how well the acoustic emission sensor 102 and/or the piezoelectric tuning fork 114 are acoustically coupled to the process control device 110. The quality factor is a ratio of energy stored within the piezoelectric tuning fork 114 as mechanical vibration to the energy dissipated by the piezoelectric tuning fork 114, which indicates the amount of damping of the piezoelectric tuning fork 114. For example, a piezoelectric tuning fork 114 with a high Q factor has low damping and a lower rate of energy loss. The Q factor may indicate a quality of the acoustic coupling between the process control device and the piezoelectric tuning fork 114 and/or the acoustic emission sensor 102. For example, if the Q factor shifts from a low Q factor to a high Q factor, the coupling between the process control device and the piezoelectric tuning fork 114 and/or the acoustic emission sensor 102 may be considered poor.

In some examples, the acoustic signal generated by the piezoelectric tuning fork 114 is increased by partially or fully immersing the piezoelectric tuning fork 114 in a fluid. For example, the housing of the piezoelectric tuning fork 114 containing the quartz crystal is filled with fluid to modify the characteristics of the quartz crystal. The viscosity of the fluid may be selected to increase the acoustic signal output by the piezoelectric tuning fork 114 such that the acoustic emission sensor 102 can detect the acoustic signal. Alternatively, the viscosity of the fluid is determined based on a coupling constant of the piezoelectric tuning fork 114 (e.g., an elastic constant related to coupling between the tines of the piezoelectric tuning fork 114) and/or an acoustic wave generation efficiency (e.g., wave generation with minimal dissipation of the acoustic signals from the piezoelectric tuning fork 114 due to direct heat or non-propagating vibration). For example, the viscosity of the fluid is selected to maximize the acoustic wave generation efficiency (e.g., the energy actually being transmitted to the acoustic emission sensor 102). The viscosity of the selected fluid may be any appropriate viscosity to maximize the acoustic wave generation efficiency. In some examples, inefficient acoustic waves are the result of energy loss (e.g., heat energy loss, non-propagating vibration) from the piezoelectric tuning fork 114. The acoustic wave generation efficiency may be determined to estimate the amount of acoustic energy traveling to the acoustic emission sensor 102 from the piezoelectric tuning fork 114.

While an example manner of implementing the example apparatus 100 is illustrated in FIG. 1, one or more of the elements, processes and/or devices illustrated in FIG. 1 may be combined, divided, re-arranged, omitted, eliminated and/or implemented in any other way. Further, the example acoustic emission sensor 102, the example piezoelectric tuning fork 114, the example controller 116, and the example operator workstation 118 may be implemented by hardware, software, firmware and/or any combination of hardware, software and/or firmware. Thus, for example, any of the example acoustic emission sensor 102, the example piezoelectric tuning fork 114, the example controller 116, and the example operator workstation 118 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example acoustic emission sensor 102, the example piezoelectric tuning fork 114, the example controller 116, and the example operator workstation 118 is/are hereby expressly defined to include a tangible computer readable storage device or storage disk such as a memory, a digital versatile disk (DVD), a compact disk (CD), a Blu-ray disk, etc. storing the software and/or firmware. Further still, the example apparatus 100 of FIG. 1 may include one or more elements, processes and/or devices in addition to, or instead of, those illustrated in FIG. 1, and/or may include more than one of any or all of the illustrated elements, processes and devices.

Figure 2:
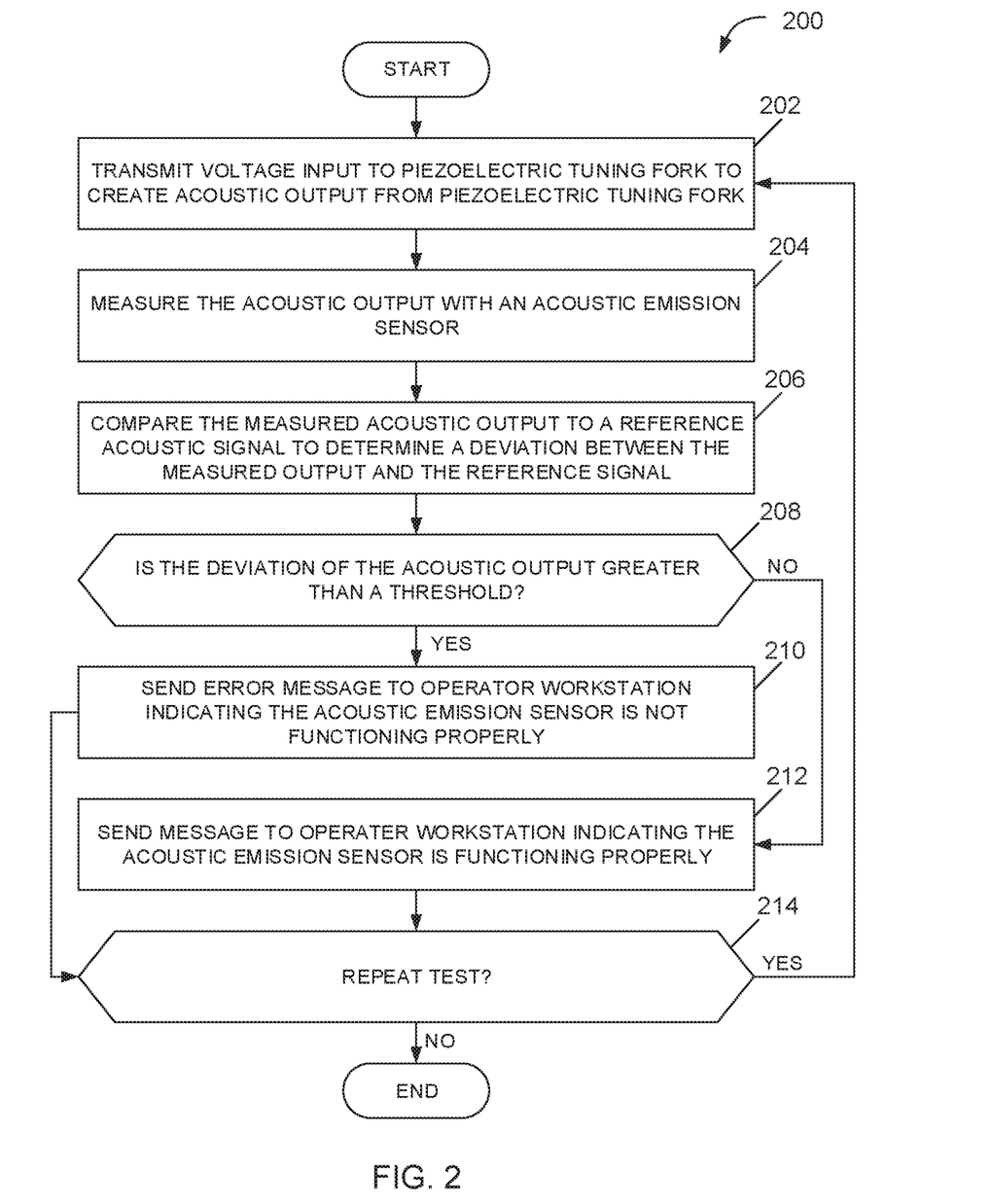
FIG. 2 depicts an example flowchart representative of a method that may be used to implement the example apparatus described herein.

A flowchart representative of an example method to implement apparatus 100 of FIG. 1 is shown in FIG. 2. In this example, the method may be implemented using, the machine readable instructions that comprise a program for execution by a processor such as the processor 312 shown in the example processor platform 300 discussed below in connection with FIG. 3. The program may be embodied in software stored on a tangible computer readable storage medium such as a CD-ROM, a floppy disk, a hard drive, a digital versatile disk (DVD), a Blu-ray disk, or a memory associated with the processor 312, but the entire program and/or parts thereof could alternatively be executed by a device other than the processor 312 and/or embodied in firmware or dedicated hardware. Further, although the example program is described with reference to the flowchart illustrated in FIG. 3, many other methods of implementing the example apparatus 100 may alternatively be used. For example, the order of execution of the blocks may be changed, and/or some of the blocks described may be changed, eliminated, or combined.

As mentioned above, the example method of FIG. 2 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and transmission media. As used herein, "tangible computer readable storage medium" and "tangible machine readable storage medium" are used interchangeably. Additionally or alternatively, the example method of FIG. 2 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and transmission media. As used herein, when the phrase "at least" is used as the transition term in a preamble of a claim, it is open-ended in the same manner as the term "comprising" is open ended.

The example method 200 of FIG. 2 begins when a voltage signal is transmitted to the piezoelectric tuning fork 114 from the controller 116 and/or the operator workstation to create an acoustic output signal from the piezoelectric tuning fork 114 (block 202). The acoustic output from the piezoelectric tuning fork 114 is measured using the acoustic emission sensor 102 (block 204). The acoustic signal measured by the acoustic emission sensor 102 and the acoustic signal output by the piezoelectric tuning fork 114 are compared to determine a deviation between the two acoustic signals (block 206). If the deviation of the acoustic signal is greater than a threshold (block 208), a diagnostic message (e.g., an alarm) is sent to the operator via the operator workstation 118 to indicate an operational condition of the acoustic emission sensor 102 (e.g., not functioning properly) (block 210). If the deviation is not greater than the threshold (block 208), a message may be sent to the operator workstation 118 indicating that the acoustic emission sensor 102 is functioning properly (block 212). The controller 116 then determines whether or not to repeat a test based on an input from the operator and/or a testing schedule (block 214). If the test is repeated, the control returns to block 202.

Figure 3:
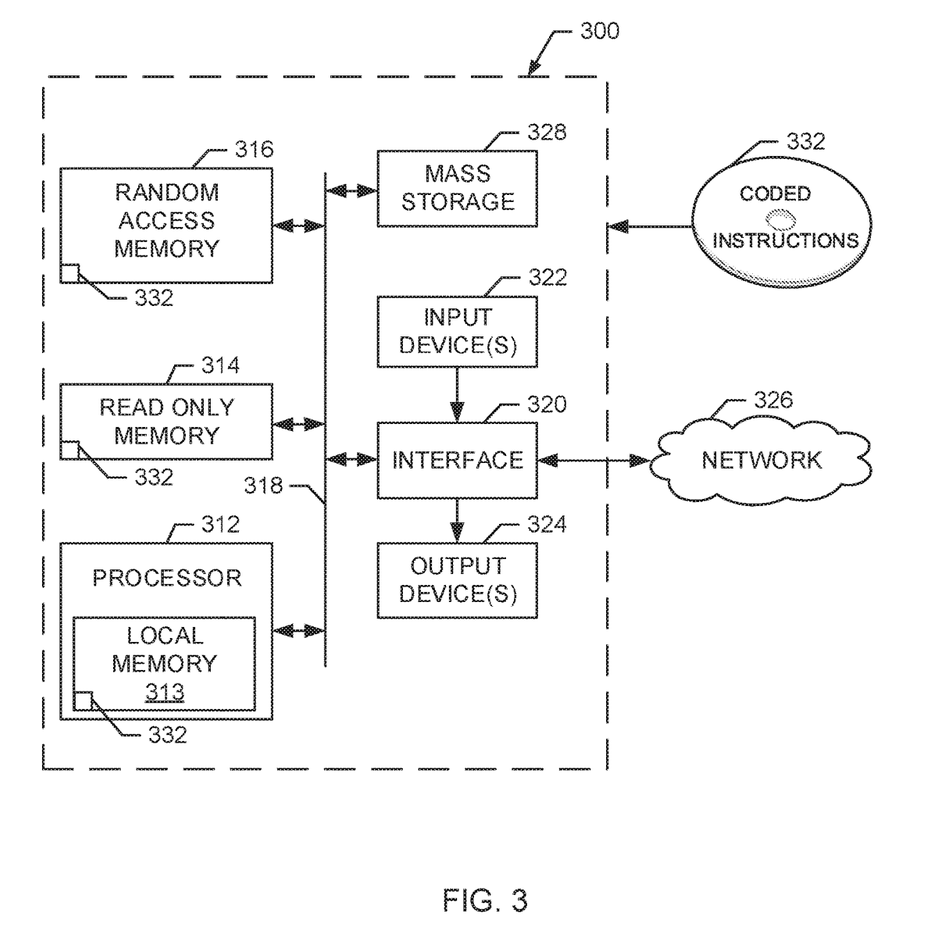
FIG. 3 is a diagram of a processor platform to execute instructions to implement the method of FIG. 2 and/or the example apparatus described herein.

FIG. 3 is a block diagram of an example processor platform 300 capable of executing instructions to implement the method of FIG. 2 and the apparatus 100 of FIG. 1. The processor platform 300 can be, for example, a server, a personal computer, a mobile device (e.g., a cell phone, a smart phone, a tablet such as an iPad™), a personal digital assistant (PDA), an Internet appliance, a DVD player, a CD player, a digital video recorder, a Blu-ray player, a gaming console, a personal video recorder, a set top box, or any other type of computing device.

The processor platform 300 of the illustrated example includes a processor 312. The processor 312 of the illustrated example is hardware. For example, the processor 312 can be implemented by one or more integrated circuits, logic circuits, microprocessors or controllers from any desired family or manufacturer.

The processor 312 of the illustrated example includes a local memory 313 (e.g., a cache). The processor 312 of the illustrated example is in communication with a main memory including a volatile memory 314 and a non-volatile memory 316 via a bus 318. The volatile memory 314 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 316 may be implemented by flash memory and/or any other desired type of memory device. Access to the main memory 314, 316 is controlled by a memory controller.

The processor platform 300 of the illustrated example also includes an interface circuit 320. The interface circuit 320 may be implemented by any type of interface standard, such as an Ethernet interface, a universal serial bus (USB), and/or a PCI express interface.

In the illustrated example, one or more input devices 1022 are connected to the interface circuit 320. The input device(s) 322 permit(s) a user to enter data and commands into the processor 312. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 324 are also connected to the interface circuit 320 of the illustrated example. The output devices 324 can be implemented, for example, by display devices (e.g., a light emitting diode (LED), an organic light emitting diode (OLED), a liquid crystal display, a cathode ray tube display (CRT), a touchscreen, a tactile output device, a light emitting diode (LED), a printer and/or speakers). The interface circuit 320 of the illustrated example, thus, typically includes a graphics driver card, a graphics driver chip or a graphics driver processor.

The interface circuit 320 of the illustrated example also includes a communication device such as a transmitter, a receiver, a transceiver, a modem and/or network interface card to facilitate exchange of data with external machines (e.g., computing devices of any kind) via a network 326 (e.g., an Ethernet connection, a digital subscriber line (DSL), a telephone line, coaxial cable, a cellular telephone system, etc.).

The processor platform 300 of the illustrated example also includes one or more mass storage devices 328 for storing software and/or data. Examples of such mass storage devices 328 include floppy disk drives, hard drive disks, compact disk drives, Blu-ray disk drives, RAID systems, and digital versatile disk (DVD) drives.

Coded instructions 332 to implement the method of FIG. 2 may be stored in the mass storage device 328, in the volatile memory 314, in the non-volatile memory 316, and/or on a removable tangible computer readable storage medium such as a CD or DVD From the foregoing, it will be appreciated that the above disclosed methods, apparatus and articles of manufacture enable an operator to obtain consistent test results of an acoustic emission sensor 102 using a testing apparatus (e.g., the piezoelectric tuning fork 114) that can be controlled remotely (e.g., from the operator workstation 118).

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. An apparatus comprising:
   a process control device;
   an acoustic emission sensor coupled to a surface of the process control device, the acoustic emission sensor to detect an operational condition of the process control device;
   a piezoelectric tuning fork coupled to the surface of the process control device and acoustically coupled to the acoustic emission sensor, the piezoelectric tuning fork to produce an acoustic signal detectable by the acoustic emission sensor, the produced acoustic signal being repeatable, the piezoelectric tuning fork to test an operational condition of the acoustic emission sensor; and
   a controller operatively coupled to the piezoelectric tuning fork, the controller to transmit an electrical signal to the piezoelectric tuning fork to cause the piezoelectric tuning fork to produce the acoustic signal.

2. The apparatus of claim 1, wherein the acoustic emission sensor includes a wear plate coupled to the surface of the process control device, the wear plate to provide an acoustic path between the process control device and the acoustic emission sensor.

3. The apparatus of claim 2, wherein the wear plate is coupled to the surface of the process control device via a liquid or gel.

4. The apparatus of claim 2, wherein the wear plate is coupled to the surface of the process control device using a glue or partial glue-filler.

5. The apparatus of claim 2, wherein the piezoelectric tuning fork is coupled to the surface of the process control device adjacent the wear plate to provide an acoustic path between the piezoelectric tuning fork and the acoustic emission sensor.

6. The apparatus of claim 1, wherein the controller is remotely located from an operator workstation that is operative to initiate a diagnostic test of the acoustic emission sensor.

7. The apparatus of claim 1, wherein the acoustic emission sensor is coupled to the surface of the process control device via a first coupling agent, and the piezoelectric tuning fork is coupled to the surface of the process control device via a second coupling agent.

8. The apparatus of claim 7, wherein the first coupling agent is formed from a same material as the second coupling agent.

9. The apparatus of claim 7, wherein first coupling agent is separated from the second coupling agent.

10. The apparatus of claim 9, wherein an acoustic path is formed from the piezoelectric tuning fork through the second coupling agent to the surface of the process control device, along the surface of the process control device between the second coupling agent and the first coupling agent, and from the surface of the process control device through the first coupling agent to the acoustic emission sensor.

11. A method comprising:
    transmitting an electrical signal from a controller to a piezoelectric tuning fork to cause the piezoelectric tuning fork to produce an acoustic signal, the piezoelectric tuning fork being coupled to a surface of a process control device and acoustically coupled to an acoustic emission sensor coupled to the surface of the process control device, the produced acoustic signal being repeatable;
    measuring the produced acoustic signal using the acoustic emission sensor; and
    comparing the measured acoustic signal to data representing a reference acoustic signal to determine a deviation between the measured acoustic signal and the reference acoustic signal.

12. The method of claim 11, further comprising determining a functionality of the acoustic emission sensor based on the deviation between the measured acoustic signal and the reference acoustic signal.

13. The method of claim 12, further comprising transmitting a message to an operator workstation operatively coupled to the acoustic emission sensor, the message indicating the functionality of the acoustic emission sensor.

14. The method of claim 11, wherein the transmitting of the electrical signal from the controller to the piezoelectric tuning fork is based on input received at the controller from an operator workstation operatively coupled to the controller.

15. The method of claim 11, wherein the transmitting of the electrical signal from the controller to the piezoelectric tuning fork occurs at a scheduled time.

16. The method of claim 11, wherein the transmitting of the electrical signal from the controller to the piezoelectric tuning fork includes transmitting electrical pulses for a time period specified by an operator workstation operatively coupled to the controller.

17. The method of claim 11, further comprising comparing the deviation between the measured acoustic signal and the reference acoustic signal to a threshold value.

18. The method of claim 17, further comprising indicating the acoustic emission sensor is functional if the deviation is less than the threshold and otherwise indicating that the acoustic emission sensor is not functional.

19. The method of claim 11, further comprising filtering the measured acoustic signal based on a quality factor and a frequency band associated with the piezoelectric tuning fork.

20. The method of claim 19, further comprising determining a quality of the acoustic coupling between the acoustic emission sensor and the process control device based on the quality factor.

* * * * *